(12) United States Patent
Funka-Lea et al.

(10) Patent No.: US 11,806,189 B2
(45) Date of Patent: Nov. 7, 2023

(54) THREE-DIMENSIONAL SEGMENTATION FROM TWO-DIMENSIONAL INTRACARDIAC ECHOCARDIOGRAPHY IMAGING

(71) Applicant: Siemens Medical Solutions USA, Inc., Malvern, PA (US)

(72) Inventors: Gareth Funka-Lea, Princeton, NJ (US); Haofu Liao, Rochester, NY (US); Shaohua Kevin Zhou, Princeton, NJ (US); Yefeng Zheng, Princeton Junction, NJ (US); Yucheng Tang, Nashville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 18/059,042

(22) Filed: Nov. 28, 2022

(65) Prior Publication Data

US 2023/0113154 A1 Apr. 13, 2023

Related U.S. Application Data

(63) Continuation of application No. 16/130,320, filed on Sep. 13, 2018, now Pat. No. 11,534,136.
(Continued)

(51) Int. Cl.
*G06K 9/00* (2022.01)
*A61B 8/08* (2006.01)
(Continued)

(52) U.S. Cl.
CPC ............. *A61B 8/0883* (2013.01); *A61B 8/12* (2013.01); *A61B 8/13* (2013.01); *A61B 8/145* (2013.01);
(Continued)

(58) Field of Classification Search
CPC ..... G06T 7/10–194; G06T 2207/20021; G06T 2207/20112–20168; G06T 2200/04;
(Continued)

(56) References Cited

U.S. PATENT DOCUMENTS 10,531,807 B2 * 1/2020 Dehghan Marvast ....................... G06V 10/454
10,540,578 B2 * 1/2020 Madani ................ G06V 10/774
(Continued)

OTHER PUBLICATIONS

Allan, G., Nouranian, S., Tsang, T., Seitel, A., Mirian, M., Jue, J., Hawley, D., Fleming, S., Gin, K., Swift, J., et al.: Simultaneous analysis of 2D echo views for left atrial segmentation and disease detection. IEEE TMI 36(1), 40(50 (2017).
(Continued)

*Primary Examiner* — Atiba O Fitzpatrick

(57) ABSTRACT

For three-dimensional segmentation from two-dimensional intracardiac echocardiography imaging, the three-dimension segmentation is output by a machine-learnt multi-task generator. Rather than the brute force approach of training the generator from 2D ICE images to output a 2D segmentation, the generator is trained from 3D information, such as a sparse ICE volume assembled from the 2D ICE images. Where sufficient ground truth data is not available, computed tomography or magnetic resonance data may be used as the ground truth for the sample sparse ICE volumes. The generator is trained to output both the 3D segmentation and a complete volume (i.e., more voxels represented than in the sparse ICE volume). The 3D segmentation may be further used to project to 2D as an input with an ICE image to another network trained to output a 2D segmentation for the ICE image. Display of the 3D segmentation and/or 2D segmentation may guide ablation of tissue in the patient.

4 Claims, 7 Drawing Sheets

Related U.S. Application Data

(60) Provisional application No. 62/634,935, filed on Feb. 26, 2018.

(51) Int. Cl.

| | |
|---|---|
| A61B 8/12 | (2006.01) |
| A61B 8/14 | (2006.01) |
| A61B 90/00 | (2016.01) |
| A61B 8/13 | (2006.01) |
| G06T 15/20 | (2011.01) |
| A61B 18/14 | (2006.01) |
| G06T 7/12 | (2017.01) |
| G06T 7/33 | (2017.01) |
| G06T 13/20 | (2011.01) |
| A61B 5/055 | (2006.01) |
| A61B 8/00 | (2006.01) |
| A61B 18/00 | (2006.01) |

(52) U.S. Cl.
CPC ............ *A61B 8/483* (2013.01); *A61B 8/5207* (2013.01); *A61B 8/5215* (2013.01); *A61B 8/5261* (2013.01); *A61B 90/37* (2016.02); *G06T 15/205* (2013.01); *A61B 5/055* (2013.01); *A61B 8/0891* (2013.01); *A61B 8/4245* (2013.01); *A61B 8/4254* (2013.01); *A61B 8/4483* (2013.01); *A61B 8/466* (2013.01); *A61B 18/1492* (2013.01); *A61B 2018/00357* (2013.01); *A61B 2018/00577* (2013.01); *A61B 2090/363* (2016.02); *A61B 2090/367* (2016.02); *A61B 2090/378* (2016.02); *A61B 2090/3762* (2016.02); *G06T 7/12* (2017.01); *G06T 7/344* (2017.01); *G06T 13/20* (2013.01); *G06T 2200/08* (2013.01); *G06T 2207/10132* (2013.01); *G06T 2207/10136* (2013.01); *G06T 2207/20004* (2013.01); *G06T 2207/20081* (2013.01); *G06T 2207/20084* (2013.01); *G06T 2207/30048* (2013.01)

(58) Field of Classification Search
CPC ....... G06T 2200/08; G06T 2207/20081; G06T 2207/20084; G06T 7/0012–0016; G06T 2207/10064–10136; G06T 2207/30004–30104; A61B 5/7485; A61B 5/0044; A61B 8/0883; A61B 8/0891; A61B 6/503; A61B 6/504; A61B 2090/378; A61B 8/12; A61B 8/4245; A61B 8/4263; A61B 8/44; A61B 8/4444; A61B 8/4477; A61B 2090/367; A61B 8/4254; G06V 10/25–273; G06V 20/49; G06V 20/695; G06V 40/162; G06V 20/80; G06V 20/698; G06V 2201/031; G06V 10/70; G06V 10/82; G06V 10/774–7796; G06V 2201/03–034; G06K 9/6224; G06K 9/6256; G06K 9/6257; G06K 9/6259; G06N 3/088; G06N 3/094; G06N 3/02–126; G06N 20/00–20; G06F 18/214–2155; G06F 7/023; G06F 40/16
See application file for complete search history.

(56) References Cited

U.S. PATENT DOCUMENTS

| | | | | |
|---|---|---|---|---|
| 10,871,536 | B2* | 12/2020 | Golden | ................. G06N 3/084 |
| 2003/0161520 | A1 | 8/2003 | Yamano et al. | |
| 2008/0101676 | A1 | 5/2008 | Zheng et al. | |
| 2008/0119727 | A1 | 5/2008 | Barbagli et al. | |
| 2017/0372193 | A1* | 12/2017 | Mailhe | ................... G06T 5/005 |
| 2019/0139641 | A1* | 5/2019 | Itu | ........................... G06N 3/045 |
| 2019/0198156 | A1 | 6/2019 | Madani et al. | |
| 2019/0205766 | A1* | 7/2019 | Krebs | ................. G06F 18/2413 |
| 2019/0223725 | A1* | 7/2019 | Lu | ........................... G06N 3/044 |
| 2019/0388064 | A1* | 12/2019 | Kezurer | ............... A61B 8/5207 |
| 2021/0204856 | A1* | 7/2021 | Dehghan Marvast | ...................... G06V 10/454 |
| 2021/0209766 | A1* | 7/2021 | Cho | ........................ G06N 3/088 |
| 2022/0076075 | A1* | 3/2022 | Madani | ............... G06F 18/2155 |
| 2023/0104045 | A1* | 4/2023 | Kezurer | ............... A61B 8/5207 382/128 |

OTHER PUBLICATIONS

Bartel, T., Müller, S., Biviano, A., Hahn, R.T.: Why is intracardiac echocardiography helpful? Benefits, costs, and how to learn. European Heart Journal 35(2), 69-76 (2013).

Caruana, R.: Multitask learning. In: Learning to learn, pp. 95{133. Springer (1998).

Chartsias A., Joyce T., Dharmakumar R., Tsaftaris S.A. (2017) Adversarial Image Synthesis for Unpaired Multi-modal Cardiac Data. In: Tsaftaris S., Gooya A., Frangi A., Prince J. (eds) Simulation and Synthesis in Medical Imaging. SASHIMI 2017. Lecture Notes inbrComputer Science, vol. 10557. Springer, Cham.

Isola, P., Zhu, J.Y., Zhou, T., Efros, A.A.: Image-to-image translation with conditional adversarial networks. In: Proc. CVPR. pp. 1125-1134 (2017).

Lin, N., Yu, W., Duncan, J.S.: Combinative multi-scale level set framework for echo image segmentation. Medical Image Analysis 7(4), 529{537 (2003).

Liu, Ming-Yu., Tuzel, Oneel., (2016) Coupled Generative Adversarial Networks. Cornell University, vol. 2.

Nie D. et al. (2017) Medical Image Synthesis with Context-Aware Generative Adversarial Networks. In: Descoteaux M. Maier-HeinbrL., Franz A., Jannin P., Collins D., Duchesne S. (eds) Medical Image Computing and Computer Assisted Intervention—MICCAIbr2017. MICCAI 2017. Lecture Notes in Computer Science, vol. 10435.

Odena, Augustus, Christopher Olah, and Jonathon Shlens. "Conditional image synthesis with auxiliary classifier gans." International conference on machine learning. PMLR, 2017.

Pathak, D., Krahenbuhl, P., Donahue, J., Darrell, T., Efros, A.A.: Context encoders: Feature learning by inpainting. In: Proc. CVPR. pp. 2536-2544 (2016).

Ronneberger, O., Fischer, P., Brox, T.: U-net: Convolutional networks for biomedical image segmentation. In: Proc. MICCAI. pp. 234{241. Springer (2015).

Ruder, Sebastian. "An overview of multi-task learning in deep neural networks." arXiv preprint arXiv: 1706.05098 (2017) (Year:br2017).

Sanchez-Quintana, D., Lopez-Minguez, J.R., Macias, Y., Cabrera, J.A., Saremi, F.: Left atrial anatomy relevant to catheter ablation. Cardiology Research and Practice (2014).

Sarti, A., Corsi, C., Mazzini, E., Lamberti, C.: Maximum likelihood segmentation of ultrasound images with rayleigh distribution. IEEE Transactions on Ultrasonics, Ferroelectrics, and Frequency Control 52(6), 947-960 (2005).

Schönemann, P.H.: A generalized solution of the orthogonal procrustes problem. Psychometrika 31(1), 1-10 (1966).

Xu, Yan, et al. "Deep learning of feature representation with multiple instance learning for medical image analysis." Acoustics, Speech and Signal Processing (ICASSP), 2014 IEEE International Conference on. IEEE, 2014.

Zhou, S.K.: Shape regression machine and efficient segmentation of left ventricle endocardium from 2D B-mode echocardiogram. Medical Image Analysis 14(4), 563-581 (2010).

Zoni-Berisso, M., Lercari, F., Carazza, T., Domenicucci, S.: Epidemiology of atrial fibrillation: European perspective. Clinical Epidemiology 6, 21320 (2014).

Spiclin, Ziga et al: "Fast and robust 3D to 2D image registration by backprojection of gradient covariances"; International Workshop on Biomedical Image Registration; Springer, Cham. 2014 (Year: 2014).

(56) References Cited

OTHER PUBLICATIONS

Wang, Jifeng et al: "Stacked conditional generative adversarial networks for jointly learning shadow detection and shadow removal"; Proceedings of the IEEE Conference on Computer Vision and Pattern Recognition. 2018 (Year: 2018).

* cited by examiner

THREE-DIMENSIONAL SEGMENTATION FROM TWO-DIMENSIONAL INTRACARDIAC ECHOCARDIOGRAPHY IMAGING

RELATED APPLICATION

This application is a continuation under 37 C.F.R. § 1.53(b) of U.S. patent application Ser. No. 16/130,320 filed Sep. 13, 2018, now U.S. Pat. No. 11,534,136, which claims the benefit of the filing date under 35 U.S.C. § 119(e) of Provisional U.S. Patent Application Ser. No. 62/634,935, filed Feb. 26, 2018, both of which are hereby incorporated by reference.

BACKGROUND

The present embodiments relate to segmentation in medical imaging to guide treatment of atrial fibrillation or other procedures. To treat atrial fibrillation, catheter ablation destroys the atypical tissues that trigger the abnormal heart rhythm. During catheter ablation, intracardiac echocardiography (ICE) is often used to guide the intervention. Compared with other imaging modalities such as transesophageal echocardiography, ICE provides better patient tolerance, requiring no general anesthesia.

Some gross morphological and architectural features of the left atrium (LA) are important to atrial fibrillation interventions. Due to the limitations of two-dimensional (2D) ICE and the difficulty in manual manipulation of the ICE transducer, these three-dimensional (3D) anatomical structures may not be sufficiently observed in certain views. This introduces difficulties to electrophysiologists as well as echocardiography image analysis algorithms that attempt automatic multi-component contouring or segmentation.

Existing approaches to 2D echocardiogram segmentation focus on a single cardiac chamber, such as the left ventricle or atrium. The segmentation distinguishes between the blood tissues and the endocardial structures. For multiple cardiac components (e.g., chambers and their surrounding structures) where the boundaries may not be clearly recognized, these 2D segmentation methods may fail. Recently, deep convolutional neural networks (CNNs) have achieved unprecedented success in medical image analysis, including segmentation. However, training a CNN to directly generate segmentation masks from 2D ICE images does not demonstrate satisfactory performance, especially for the less-observed pulmonary veins. Such a baseline solely relies on the brute force of big data to cover all possible variations, which is difficult to achieve.

SUMMARY

Systems, methods, and instructions on computer readable media are provided for three-dimensional segmentation from two-dimensional intracardiac echocardiography imaging. The three-dimension segmentation is output by a machine-learnt multi-task generator. Rather than the brute force approach of training the generator from 2D ICE images to output a 2D segmentation, the generator is trained from 3D information, such as a sparse ICE volume assembled from the 2D ICE images. Where sufficient ground truth data is not available, computed tomography or magnetic resonance data may be used as the ground truth for the sample sparse ICE volumes. The generator is trained to output both the 3D segmentation and a complete volume (i.e., more voxels represented than in the sparse ICE volume). The 3D segmentation may be further used to project to 2D as an input with an ICE image to another network trained to output a 2D segmentation for the ICE image. Display of the 3D segmentation and/or 2D segmentation may guide ablation of tissue in the patient.

In a first aspect, a method is provided for three-dimensional segmentation from two-dimensional intracardiac echocardiography imaging in a medical imaging system. Positions of scan planes within a of a patient are sensed for the intracardiac echocardiography (ICE) imaging. An ICE volume is formed from ultrasound data for the scan planes from the positions. The three-dimensional segmentation is generated from input of the ICE volume to a machine-learned multi-task generator having been trained adversarially with first and second discriminators. The first discriminator is for the three-dimensional segmentation. An image of the three-dimensional segmentation is displayed.

In a second aspect, a method is provided for machine training of three-dimensional segmentation from two-dimensional intracardiac echocardiography imaging. A multi-task generative adversarial network is defined to have output layers for volume completion and three-dimensional segmentation. Computed tomography or magnetic resonance volumes from a first group of patients are assigned as ground truth volumes for ultrasound imaging of a second group of patients. The multi-task generative adversarial network is machine trained to generate first volumes and three-dimensional segments from input ultrasound volumes assembled from planar images. The training is based on the assigned ground truth volumes. A generator of the machine-trained multi-task generative adversarial network is stored.

In a third aspect, a medical imaging system is provided for three-dimensional segmentation from two-dimensional intracardiac echocardiography imaging in ablation. An ultrasound imager is configured to generate two-dimensional images ICE images of a cardiac system of a patient with the ICE transducer. An image processor is configured to generate the three-dimensional segmentation from the two-dimensional ICE images with a machine-learned generative network. A display is configured to display ablation guidance relative to an image of the three-dimensional segmentation.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Knowledge is integrated to boost contouring performance. Such knowledge stems from two sources: (i) 3D geometry information provided by a position sensor embedded inside an ICE catheter and 3D image appearance information exemplified by cross-modality computed tomography (CT) or magnetic resonance (MR) volumes that contain the same anatomical structures. The knowledge may be integrated from both sources with machine learning for a multi-task network to provide cross-modality volume completion and 3D+2D segmentation for intracardiac echocardiography contouring. The ICE information in 3D allows for at least an initial 3D contour, making the 2D contour more accurate. The use of a full or complete volume provided by the other modality assists in making the 3D contour more accurate. By performing both completion and 3D segmentation in one multi-task network, the resulting segmentation may be more accurate.

3D or 2D contouring may be provided despite the sparseness and noise in imaging with planar ICE images. Catheter ablation to treat atrial fibrillation increasingly relies on ICE for an anatomical delineation of the left atrium or ventricle of the heart and the pulmonary veins or other vessels that connect with the atrium or ventricle. It is a challenge to build an automatic contouring algorithm because ICE is noisy and provides only limited 2D views of the 3D anatomy. For an automatic solution to segment anatomy from ICE, the cross-modality solution leverages a database of diagnostic non-ultrasound images to supplement the less available interventional images.

In one embodiment, a deep neural network uses 3D geometrical information provided by a position sensor embedded in the ICE catheter and 3D image appearance information from a set of CT or MR cardiac volumes. The approach starts by using the 3D position information to form a 3D sparse volume based on the 2D ICE images. To leverage 3D image appearance information, the system performs a combined cross-modality volume completion to generate a pseudo CT or MR volume and generates a 3D segmentation. This achieves a collaborative structural understanding through a multi-task, volume-to-volume network with an adversarial formulation. In an additional step, an additional neural network generates a refined 2D segmentation taking as input both an original ICE image and a preliminary 2D segmentation projected from the 3D segmentation.

Figure 1:
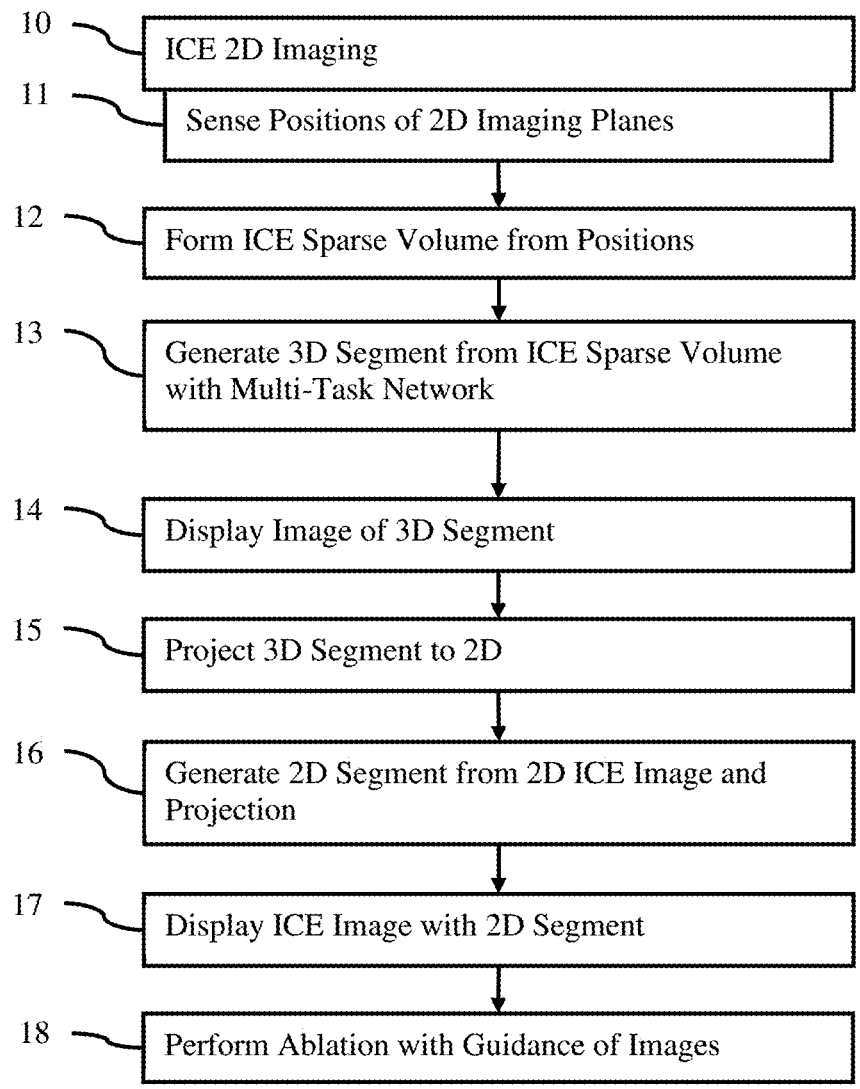
FIG. 1 is a flow chart diagram of one embodiment of a method for 3D segmentation from 2D intracardiac echocardiography imaging in a medical imaging system.

FIG. 1 is a flow chart diagram of one embodiment of a method for three-dimensional segmentation from two-dimensional intracardiac echocardiography imaging in a medical imaging system. Using 3D geometry knowledge from the position sensor, a 3D sparse volume based on the 2D ICE images is formed. Then, to tap into the 3D image appearance knowledge, a multi-task 3D network created with an adversarial formulation is applied. The network performs cross-modality volume completion and sparse volume segmentation simultaneously for collaborative structural understanding and consistency. Taking as inputs both the original 2D ICE image and the 2D mask projected from the generated 3D mask, a machine-learned network refines the 2D segmentation results.

Figure 2:
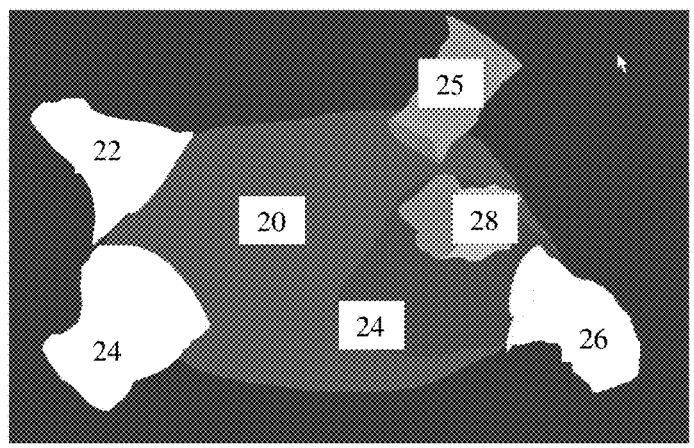
FIG. 2 illustrates example left atrium anatomy.

The context of use is for treatment of atrial fibrillation under the guidance of ICE imaging. The left atrium may be the most common anatomy of interest for this context. FIG. 2 shows an example left atrium 20 and surrounding structure of interest. The structure includes the left atrial appendage (LAA) 26, left inferior pulmonary vein (LIPV) 25, left superior pulmonary vein (LSPV) 28, right inferior pulmonary vein (RIPV) 22, and right superior pulmonary vein (RSPV) 24. Additional, different, or fewer structures or parts of interest may be included. Any of the structures may be portions, such as a root or base of a vein. The left ventricle or other heart chambers may be the anatomy of interest in other embodiments. Other ICE imaging locations may result in other anatomy of interest, such as arteries or veins. The left atrium and the corresponding anatomy are used as examples below.

The method is performed in the order shown (e.g., top to bottom or numerical), but other orders may be used. For example, the display of act 14 does not occur until the display of act 17. Act 18 may be performed as part of repetition of acts 10-17, such as associated with ongoing imaging of act 10.

Additional, different or fewer acts may be provided. For example, acts 15-17 and/or 18 are not provided. In another example, act 14 is not provided as the 3D segment may be used for act 15 without display.

The method is performed by a medical diagnostic ultrasound scanner with one or more ablation systems. An ICE catheter and corresponding transducer connect with the scanner to perform act 10. A sensor on the ICE catheter or transducer is used to perform act 11. An image processor of the scanner performs acts 12, 13, 15, and 16, but a computer or server may perform the acts. The image processor in conjunction with a display device performs acts 14 and 17. The ablation system, such as a power source connected with an electrode in the catheter or another catheter, performs act 18. Other devices may be used to perform any of the acts.

In act 10, the ultrasound scanner uses an ICE catheter to image. The transducer of the ICE catheter scans a plane. The scan plane is oriented based on a position of the catheter. As the catheter moves (e.g., translates or rotates), different scan planes are scanned. Each scan generates a frame of data representing the scan plane at that time. The frame of ultrasound data may be scalar values or display values (e.g., RGB) in a polar coordinate or Cartesian coordinate format. The frame of ultrasound data may be a B-mode, color flow, or other ultrasound image.

A sequence of frames of data result from the ICE imaging. Each frame represents a 2D scan plane, so a collection of frames representing different 2D scan planes in the volume of and/or around the heart are acquired.

In act 11, a sensor senses the positions of the scan planes. A magnetic position sensor, fiducials with x-ray or acoustic scanning, or imager with image processing determines the location and orientation of the transducer for each frame. The location and orientation define the scan plane. The position of each scan plane is sensed. Different scan planes have different positions. The positions of the scan planes within a cardiac system (e.g., heart and/or vessels) of a patient are sensed for the ICE imaging of act 10.

The scanning defines the sample locations within each scan plane. The area covered by the ultrasound scanning and the position of the area in the heart volume are determined.

In act 12, an image processor forms an ICE volume from ultrasound data for the scan planes. The known locations represented by the ultrasound data are used to populate a volume. The sensed positions are used to assign scalar or other ultrasound data to different voxels. Alternatively, the sensed positions are used to align the planar locations represented by the ultrasound data within the volume. The ultrasound data is mapped to three dimensions using the positions of the scan planes.

Figure 3:
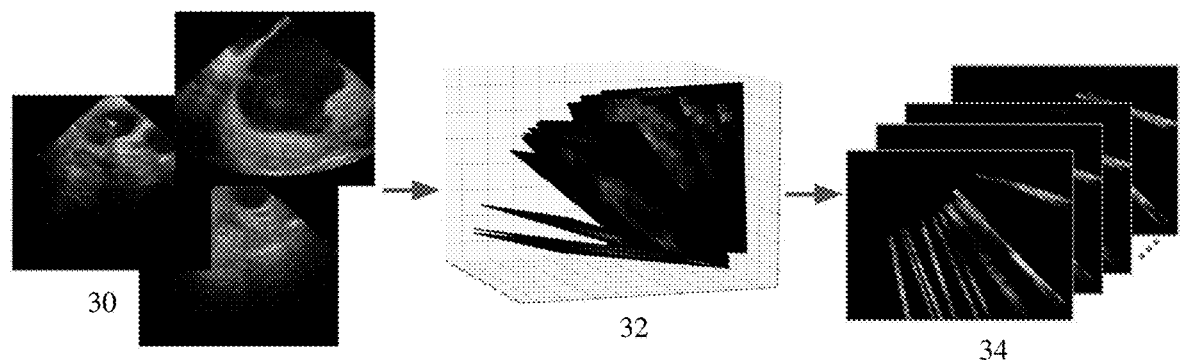
FIG. 3 illustrates an example of forming a 3D sparse ICE volume.

The mapping forms a 3D sparse ICE volume using the location information associated with each ICE image. In one embodiment shown in FIG. 3, a set of 2D ICE images 30 are input, each including part of the heart in its field of view. The sensed 3D position is used to map all the 2D ICE images 30 to 3D space 32, thus forming a sparse ICE volume 34. The generated 3D sparse ICE volume 34 keeps the spatial relationships among individual ICE views.

The volume 34 is sparse due to the incomplete sampling of all voxel locations. Due to the user guided movement of the transducer and/or heart or other patient motion, less than all the volume is sampled in ICE imaging. Some fields of view may include only one or less than all the structures of interest. Once assembled as a volume, less than all voxels may be represented by the ultrasound data. A segmentation method uses the sparse volume for better anatomical understanding and structural consistency as compared to a single 2D ICE image. Due to the sparsity and noisy nature of ultrasound data, segmentation using just the sparse ICE volume may not be as accurate as desired for diagnosis and/or guiding ablation.

In act 13, the image processor generates a 3D segmentation from input of the ICE volume 34 to a machine-learned multi-task generator. The 3D segmentation is a labeling by voxel or location of different anatomy. The anatomy represented by each location is labeled. Alternatively, the segmentation forms a 3D mesh for each anatomy. Other segmentation results may be provided. The 3D segmentation provides a boundary for one or more structures in 3D. The segmentation is of one or more structures of interest, such as identifying the locations of a sub-set or all the anatomical structures of interest discussed above for FIG. 2 for the left atrium.

The 3D segmentation uses a machine-learned network. The ICE volume with or without other data are input to the machine-learned network and multiple outputs—one a complete volume and the other a 3D segmentation—are output in response. The machine-learned network is a multi-task network.

The machine-learned network is an image-to-image network, such as a generator of a generative adversarial network (GAN), trained to convert the ICE volume to the complete volume and the 3D segmentation. For example, the trained convolution units, weights, links, and/or other characteristics of the network are applied to the data of the ICE volume and/or derived feature values to extract the corresponding features through a plurality of layers and output the complete volume and the 3D segmentation. The features of the input are extracted from the ICE images as arranged in 3D. Other more abstract features may be extracted from those extracted features using the architecture. Depending on the number and/or arrangement of units or layers, other features are extracted from the input.

Any machine training architecture for outputting a spatial distribution from an input spatial distribution may be used. For example, U-Net is used. A convolutional-to-transposed-convolutional network is used. One segment of layers or units applies convolution to increase abstractness or compression. The most abstract feature values are then output to another segment. The other segment of layers or units then applies transposed-convolution to decrease abstractness or compression, resulting in outputting of an indication of class membership by location. The architecture may be a fully convolutional network.

A GAN includes a generator, such as the image-to-image or U-Net, and two or more discriminators. A discriminator is provided for each task of the multi-task network. The generator includes an encoder (convolutional) network and decoder (transposed-convolutional) network forming a "U" shape with a connection between passing features at a greatest level of compression or abstractness from the encoder to the decoder. Skip connections may be provided. Any now known or later developed U-Net architectures may be used. Other fully convolutional networks may be used.

For application for a given patient, the generator of the GAN is used without the discriminators. The GAN are applied to the patient ICE volume by the generator without the discriminators. The discriminators are used for training.

The GAN is a deep architecture, which may include convolutional neural network (CNN) or deep belief nets (DBN). Other deep networks may be used. CNN learns feed-forward mapping functions while DBN learns a generative model of data. In addition, CNN uses shared weights for all local regions while DBN is a fully connected network (i.e., having different weights for all regions of an image). The training of CNN is entirely discriminative through back-propagation. DBN, on the other hand, employs the layer-wise unsupervised training (e.g., pre-training) followed by the discriminative refinement with back-propagation if necessary.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

Within a unit or layer, any number of nodes is provided. For example, 100 nodes are provided. Later or subsequent units may have more, fewer, or the same number of nodes. The features of the nodes are learned by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features.

Training of AE or RBM is prone to over-fitting for high-dimensional input data. Sparsity or denoising techniques (e.g., sparse denoising AE (SDAE)) are employed to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+convolution). Max pooling, upsampling, downsampling, and/or softmax layers or units may be used. Different units may be of the same or different type.

In one embodiment, the generator includes a U-Net with one or more skip connections. The skip connections 38 pass features from the encoder to the decoder at other levels of abstraction or resolution than the most abstract (i.e. other than the bottleneck). Skip connections provide more information to the decoding layers. A Fully Connected layer may be at the bottleneck of the network (i.e., between the encoder and decoder at a most abstract level of layers). The fully connected layer may make sure as much information as possible is encoded. Batch normalization may be added to stabilize the training.

The output or final layer of the architecture may form both outputs. One network may be used for both tasks. There are multiple outputs from the one network. There is one output for the segmentation of each anatomical structure and another output for the pseudo CT. One or more additional layers may be added in this framework to further process either the segmentation or pseudo CT outputs. In one embodiment, 5 down sampling blocks are followed by 5 up sampling blocks. Each down sampling block is a 3D convolution layer, followed by a batch normalization layer and a RELU layer. Each up-sampling block is a 3D deconvolution layer, followed by a batch normalization layer and a RELU layer. Skip connections are used to connect down sampling blocks and corresponding up sampling blocks. Drop out has been used. Alternatively, the output of the U-net is to two separate layers or networks. One or more layers are provided for each task. The layers for forming the complete volume from the output of the U-net are different than the layers for forming the 3D segmentation from the output of the U-net.

Figure 4:
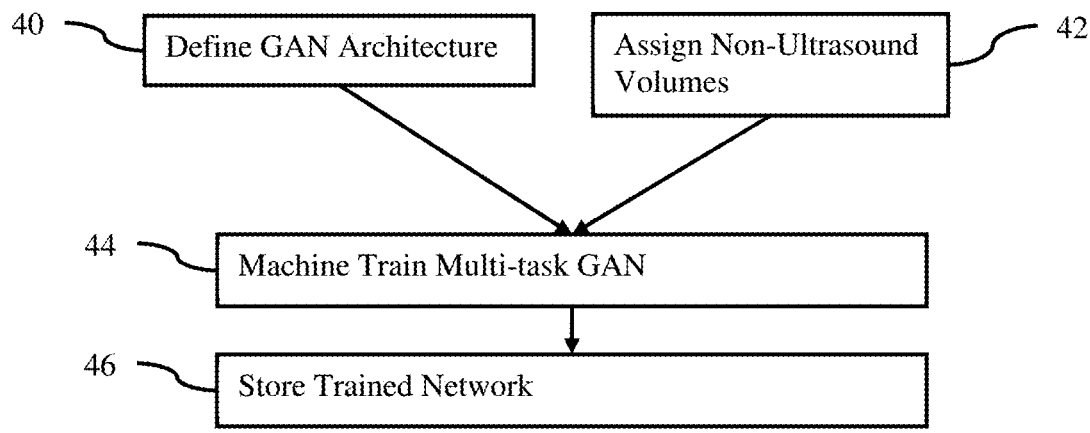
FIG. 4 is a flow chart diagram of one embodiment of a method for machine training for 3D segmentation from 2D ICE images.

FIG. 4 shows an example method for machine training of 3D segmentation from 2D ICE imaging. The method is implemented by a machine (e.g., computer, processor, workstation, or server) using training data (e.g., samples and ground truths for the samples) in a memory.

The basic approach for training a GAN is to update the discriminators with both generated and real volumes or 3D segmentations, freeze weights in the discriminator, and then update the generator on how good the generator is at fooling the discriminators. Weights in the generator are updated while minimizing the binary cross entropy or other loss of the discriminators. In one embodiment, the GAN is trained from an initial state based on noise. In another embodiment, the generator is trained from initialized or conditional values created by pre-training or other training.

In act 40, a multi-task GAN is defined. The network architecture includes output layers for both tasks, volume completion and three-dimensional segmentation. Any image-to-image or GAN network architecture may be used, such as a U-net type of arrangement with downsampling and upsampling blocks or layers with or without skip connections. For multi-task GAN, the architecture includes two or more discriminator networks or layer arrangements. A discriminator network is provided for each of volume completion and 3D segmentation.

For training the machine-learned network, the machine learning network arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

Figure 5:
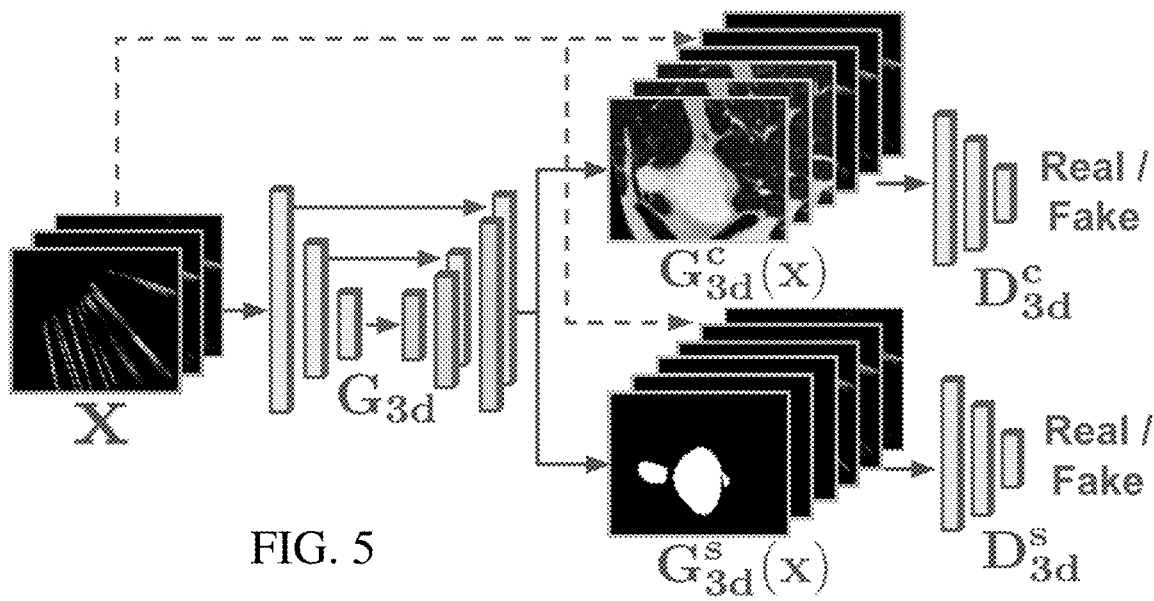
FIG. 5 shows an example multi-task generative adversarial network architecture.

FIG. 5 shows one example network architecture. The network includes a generator Gad for input and output of data representing three dimensions. The network includes two discriminators $D_{3d}^c$ and $D_{3d}^s$. The sparse ICE volume x is input to the generator and the discriminators. The generator $G_{3d}$ performs 3D segmentation and completion simultaneously and outputs a segmentation map $G_{3d}^s(x)$ as well as a denser volume $G_{3d}^c$.

During training, the ground truth of $G_{3d}^c$ is a CT or MR volume instead of a dense ICE volume. CT is used in the examples herein. A dense ICE volume may be used but are not typically available with a sufficient number of samples for machine training.

In act 42, the CT volumes from a first group of patients are assigned as ground truth volumes for ultrasound imaging of a second group of patients. The same or different CT volume is paired with different ones of the ICE volumes. The ICE images and the CT volumes are from different patients, but some of the samples for the training data may include ICE images and CT volumes from the same patients. Having the complete volume ground truth from one patient and the input sample ICE images from another patient provides for a cross-modality volume completion problem with unpaired data. Adversarial learning and pairing (e.g., mesh pairing) allow use of data from different modalities and patients.

To create samples for training, CT volumes are paired with ICE imaging samples. A collection of example CT volumes represents parts of the cardiac systems (e.g., hearts) of various patients. The CT volumes include mesh or other boundary of one or more anatomical structures, such as the left atrium. Meshes of the same anatomical structures are formed in the ICE volumes of the training samples. After Procrustes analysis, the mesh from the CT volume that is closest to a given mesh in each sample indicates the CT volume to pair with that sample. Additional samples may be formed by random perturbation in scale, rotation, and/or translation for paired samples.

The two discriminators judge the realness of the outputs from the generator. When trained adversarially together with a generator, the discriminators make sure the generator's outputs are more perceptually realistic. Following conditional GAN, the discriminators take the ICE volume x as an input to further improve adversarial training.

In one embodiment, the neural network is defined to be a 3D UNet-like network as the generator. There are 8 consecutive downsampling blocks (encoder) followed by 8 consecutive upsampling blocks (decoder) in the network. Skip connections shuttle feature maps between two symmetric blocks of the encoder and decoder at all or some levels of abstraction or resolution. Each downsampling block contains a 3D convolutional layer, a batch normalization layer, and a leaky ReLU layer. Similarly, each upsampling layer contains a 3D deconvolutional layer, a batch normalization layer and a ReLU layer. The convolutional and deconvolutional layers have the same parameter settings: 4×4×4 kernel size, 2×2×2 stride size, and 1×1×1 padding size. A tanh function is attached at the end of the generator to bound the network outputs. The two discriminators have identical network architectures with each of them having 3 downsampling blocks followed by a 3D convolutional layer and a sigmoid layer. The downsampling blocks for the discriminators are the same as the ones used in the generator. The final 3D convolutional layer (e.g., 3×3×3 kernel size, 1×1×1 stride size, and 1×1×1 padding size) and sigmoid layer are used for realness classification. Other numbers of layers or blocks, composition of each block, kernel sizes, stride sizes, padding sizes, and/or other characteristics of the architecture may be used.

In act 44, the machine (e.g., processor, computer, workstation, or server) machine trains the defined network (e.g., the defined multi-task GAN). The network is trained to generate denser or complete volumes and 3D segments from input ultrasound volumes assembled from planar images. The generator and discriminators are trained by machine learning. Based on the architecture, the generator is trained to output the complete volume and the 3D segment, and the discriminators are trained to output a determination based on the input of the complete volume and the 3D segment to the respective discriminators.

The training data includes many samples (e.g., hundreds or thousands) of ICE volumes and ground truth paired CT volumes as the complete volumes and 3D segmentations for the ICE volumes or the CT volumes. The network is trained to output based on the assigned ground truths for the volumes and segmentations.

Collaborative image inpainting (3D segmentation) is implemented in a cross-modality fashion to address the problem that data of a targeting modality is missing. 3D ultrasound data of left atrium (organ of interest) may not be available, so the CT data of the left atrium and/or 3D ultrasound left ventricle are used as the ground truth volumes. Data across different modalities and/or organs are used in the collaborative image inpainting model, allowing learning the left atrium structure and the 3D ultrasound modality at the same time. The network is trained to segment the left atrium of the 3D ICE volume even though the anatomy is provided in training from a different modality or part of the heart.

For training any of the networks, various optimizers may be used, such as Adadelta, SGD, RMSprop, or Adam. The weights of the network are randomly initialized, but another initialization may be used. End-to-end training is performed, but one or more features may be set. Batch normalization, dropout, and data augmentation are not used, but may be (e.g., using batch normalization and dropout). During the optimization, the different distinguishing features are learned. The features providing an indication of anatomy location or missing volume information given a input sparse ICE volume are learned.

The optimizer minimizes an error or loss, such as the Mean Squared Error (MSE), Huber loss, L1 loss, or L2 loss. In one embodiment, the machine training uses a combination of adversarial loss and reconstruction loss. The discriminators provide adversarial losses for the 3D segmentation and the volume completion. The reconstruction loss is a measure of difference of the 3D segmentation from the ground truth segmentation and of difference of the complete volume from the ground truth volume.

For adversarial loss Lady, the segmentation task s and completion task c are trained jointly in a multi-task learning (MTL) fashion. The adversarial loss for a task $t \in \{s, c\}$ may be written as:

$$L_{adv}^{t} = E_{x,y_t \sim p(x,y_t)}[\log D_{3d}^{t}(x,y_t)] + E_{x \sim p(x)}[1 - \log D_{3d}^{t}(x, G_{3d}^{t}(x))]$$

where p denotes the data distributions, E is the expectation, and $y_t$ is the ground truth segmentation map or CT volume. For the generated data $G^t(x)$, the discriminators learn to give a "fake" label. On the other hand, the generator $G_{3d}$ is trained to deceive by making $G^t(x)$ as "real" as possible.

Adversarial loss alone, however, may not give a strong structural regularization to the training. The reconstruction loss measures the pixel or voxel-level error between the generator outputs and the ground truths. For reconstruction loss, an error per location (e.g., voxel or mesh node) is calculated for the volume and the 3D segmentation. For the segmentation task, error per voxel is converted to a multi-channel map with each channel denoting the binary segmentation map of a target anatomy. An L2 loss between the generated output and the ground truth is calculated. For the completion task, an L1 loss is used instead of an L2 loss since L2 loss may result in overly smooth complete volumes. Other loss functions may be used.

The segmentation and completion reconstruction losses are combined. For example, a weighted average or summation is used.

The total loss is given by a combination of the reconstruction and adversarial losses. Any combination may be used, such as a weighted summation. The weighting coefficients may be selected to weight loss contribution from adversarial and reconstruction losses. The loss combinations from the 3D segmentation and the completion outputs are summed to form the total loss. Other functions may be used.

In act 46, the trained network is stored. The network parameters, such as connections, convolution kernels, weights, or other learned values for the network are stored. The network is stored in memory to be used for application or testing.

Once trained, the model may be applied to estimate a 3D segmentation and/or complete volume in act 13 of FIG. 1. The many samples in the training data are used to learn to output given an unseen sample, such as an ICE volume from a patient.

The machine-learned multi-task generator generates volume data less sparse than the ICE volume. A CT-like complete or more dense volume is generated based on input of the sparser ICE volume. The output volume has values for a larger number of voxels or greater density of voxels than the input ICE volume. The output complete or denser volume represents part of the cardiac system (e.g., heart) of the patient.

The machine-learned multi-task generator generates a 3D segmentation. The boundary or boundaries of one or more structures are output, such as LA. A mesh or voxel-by-voxel label is output. Locations associated with one or more structures of interest are output. The output is in three dimensions, providing a distribution of the boundary through a volume rather than just in a plane.

In act 14, a display displays an image of the 3D segmentation. An image of the anatomical structure of interest, such as the left atrium or ventricle with or without other structures, is generated on a display screen. The structure or structures to include may be selected by the user.

The 3D segmentation is rendered to a 2D plane. Any rendering may be used, such as surface rendering. In another embodiment, the 3D segmentation masks the complete volume. The unmasked part of the complete volume is the structure designated by the 3D segmentation. The masked volume is volume rendered to show an image of the 3D segmentation. In yet another embodiment, a slice or plane defines the part of the 3D mesh to image.

The 3D segmentation may be a mesh or other graphic for the 3D surface projected to a 2D plane defined by a viewing direction. The resulting projected graphic is displayed as the image.

The 3D segmentation may be displayed alone or with other information. For example, the complete volume is rendered to an image. The 3D segmentation and complete volume images are displayed adjacent to each other. Alternatively, the 3D segmentation as projected or rendered to 2D is overlaid on a rendering from the completed volume.

The display is a visual output. The image processor generates an image. A segmentation image is generated and displayed on the display. The image may be output to a display, into a patient medical record, and/or to a report.

In addition to or as an alternative to displaying the 3D segmentation, the 3D segmentation may be used to determine a 2D segmentation for one or more 2D ICE images. In act 15, the image processor projects the three-dimensional segmentation to a plane. The projection is along lines orthogonal to the plane. The plane is the scan plane of the 2D ICE image. The projection may be selection of the boundary of the anatomy for a planar slice at the scan plane. Alternatively, the projection is a surface rendering or volume rendering.

In act 16, the image processor generates a 2D segmentation for an ICE image. The planar or 2D ICE image and the projection from the 3D segmentation for the scan plane of the ICE image are input to a machine-learned network. For example, a generator of a conditional GAN is used as the machine-learned network. The machine-learned network outputs a 2D segmentation, such as boundaries or the 2D ICE image with highlighting by masking, color, intensity or graphic to indicate the segmentation. The contour of the anatomy of interest as shown in a plane is refined rather than using the 3D projection.

The 2D segmentation network is trained by machine learning. Training data includes many samples of ICE images, 3D segmentation projections for the images, and ground truth 2D segmentations for the ICE images.

Figure 6:
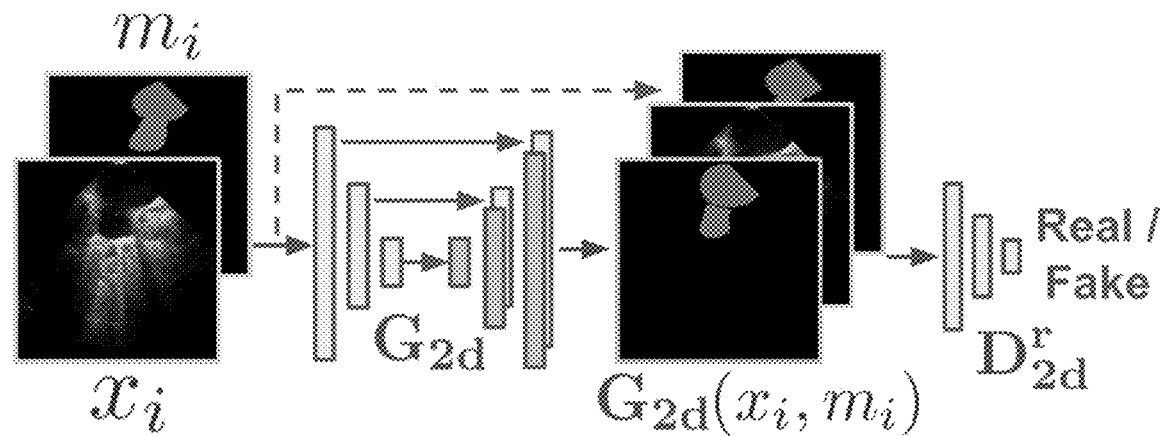
FIG. 6 shows an example generative adversarial network for 2D segmentation from a 2D ICE image and a 2D projection from a 3D segmentation.

An image-to-image network architecture is used. For example, a U-net based GAN is used, but other architectures may be used. FIG. 6 shows an example. The 2D refinement network has a similar structure as the GAN of FIG. 5 but is not a multi-task network. The generator has a same U-net layer or block structure except that the convolutional and deconvolutional layers are in 2D rather than 3D. The inputs are a 2D ICE image $x_i$ together with its corresponding 2D segmentation map $m_i$ where $m_i$ is obtained by projecting $G_{3d}^s(x)$ onto $x_i$. The training of the 2D-RefineNet is also performed in an adversarial fashion, providing the discriminator $D_{2d}^r$. The conditional GAN is used to allow the discriminator to observe the generator inputs (i.e., both inputs are also input to the discriminator).

The same loss or different loss may be used in training. For example, an adversarial loss is computed as described above and the L2 distance between the output 2D segmentation and the ground truth 2D segmentation is used for the reconstruction loss. The losses are combined as a weighted sum for the total loss. Other loss functions may be used.

In act 17, the display displays the ICE image with the 2D segmentation. The ICE image is shown with a graphic, color modulation, intensity modulation, masking, or other highlighting of locations belonging to a given anatomical structure or structures, such as the LA boundaries. Different or the same highlighting may be used for different anatomical structures.

The 2D segmentation may be combined with the 3D segmentation. For example, the ICE image with the 2D segmentation is displayed adjacent to a rendering from the 3D segmentation.

A sequence of 3D and/or 2D segmentation images may be shown. As additional ICE images are acquired, the ICE volume is updated and the 3D and 2D segmentations are output.

The segmentation uses ICE images and corresponding ICE volume from a given phase of the heart cycle. Alternatively, the machine-learned network or networks are trained to output the segmentation over time, such as different 3D and/or 2D segmentations for different phases of the heart cycle. The segmentations from other phases may be used as inputs to the machine-trained networks for predicting a current segmentation.

Acts 15-17 may be repeated for different 2D ICE images. A sequence of 2D ICE images are obtained, and the projection, segmentation, and display are performed for each.

In act 18, ablation for atrial fibrillation is performed. The electrode or other ablator is positioned adjacent tissue to be scarred or ablated. The positioning uses the 3D and/or 2D segmentation as a guide. For example, the electrode is positioned based on the 3D segmentation against the tissue to be treated. The 2D segmentation is used to confirm proper placement. Once placed, power is applied to the electrode, ablating the tissue. Only 2D or only 3D segmentation may be used to guide in other embodiments.

The method of FIG. 1 may provide better or more accurate 2D segmentation than merely segmenting the 2D ICE images directly with a machine-learned network. 5-fold cross-validation is performed using over 11,000 ICE images from 150 clinical patients. The method of FIG. 1 is better than a direct 2D image-to-image deep neural network segmentation, especially for less-observed structures.

The left atrial ICE images are collected using a clinical system with each image associated with a homogeneous matrix that projects the ICE image to a common coordinate system. Both 2D and 3D annotations are performed on the ICE images for the cardiac components of interest (e.g., LA, LAA, LIPV, LSPV, RIPV and/or RSPV). For the 2D annotations, contours of all the plausible components in the current view are annotated. For the 3D annotations, ICE images from the same patient and at the same cardiac phase are first projected to 3D, and 3D mesh models of the target components are then manually annotated. 3D segmentation masks are generated using these mesh models. For each of the 150 patients, there are 20-80 gated 2D ICE frames for use. 3D annotations are created for all 150 patients. For 2D annotations, annotations are performed for 100 patients, resulting in a total of 11,782 annotated ICE images. By anatomical components in 2D, there are 4669 LA, 1104 LAA, 1799 LIPV, 1603 LSPV, 1309 RIPV, and 1298 RSPV annotations to use as ground truth and samples. The LA is mostly observed, and the LAA and PVs are less observed. For a subset of 1568 2D ICE images, two or three expert annotations per image are created to compute inter-rater reliability (IRR).

As dense ICE volumes are not available for training, CT volumes are used instead as the ground truth for the completion task. Each CT volume is associated with a LA mesh model. To pair with a sparse ICE volume, the CT volume whose LA mesh model is closest to that of the targeting sparse ICE volume after Procrustes analysis is selected. In total, 414 CT volumes are available, which gives enough anatomical variability for the mesh pairing. All the data used for 3D training are augmented with random perturbations in scale, rotation and translation to increase the generalizability of the model.

The 3D-SCNet and 2D-RefineNet networks of FIGS. 5 and 6, respectively, are trained using Adam optimization with lr=0.005, $\beta_1$=0.5, $\beta_2$=0.999. The 3D-SCNet is trained for about 25 epochs with the adversarial loss weight for segmentation, $\lambda_{adv}^s$, =0.2, the adversarial loss weight for completion, $\lambda_{adv}^c$, =1, and with the reconstruction loss weight for segmentation, $\lambda_{rec}^s$, =1,000 and the reconstruction loss weight for completion, $\lambda_{rec}^c$, =100. The 2D-RefineNet is trained for about 25 epochs with the adversarial loss weight=1 and the reconstruction loss weight=1000. All weights are chosen empirically. The networks are trained using 5-fold cross-validation. The segmentation results are evaluated using the Dice metric and average symmetric surface distance (AASD).

Figure 7A:
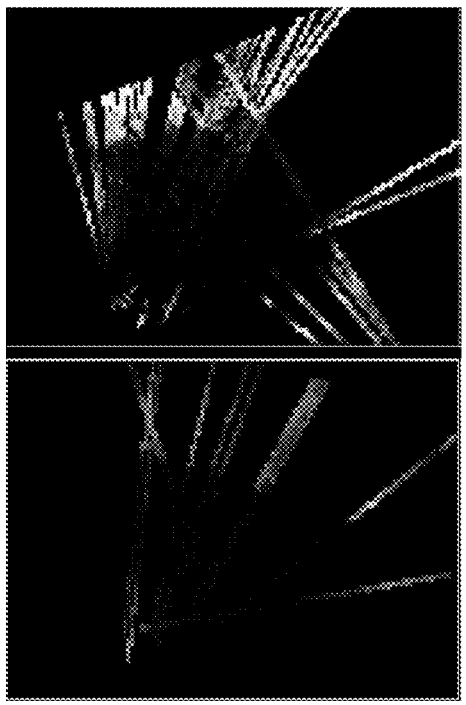
FIGS. 7A-E show example images for the 3D segmentation of FIG. 1.
Figure 7B:
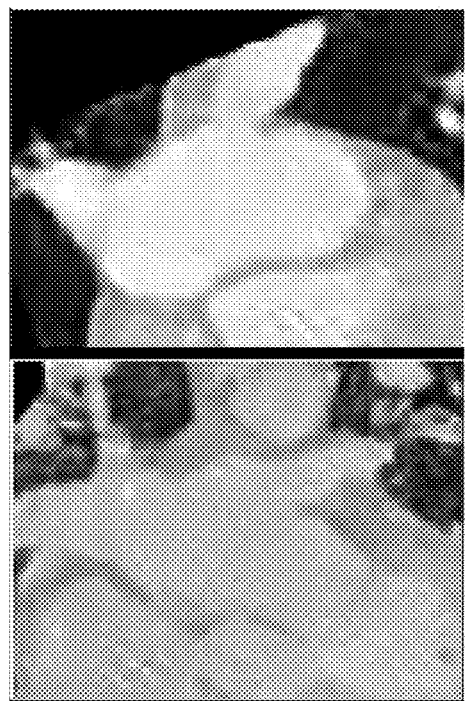
Figure 7C:
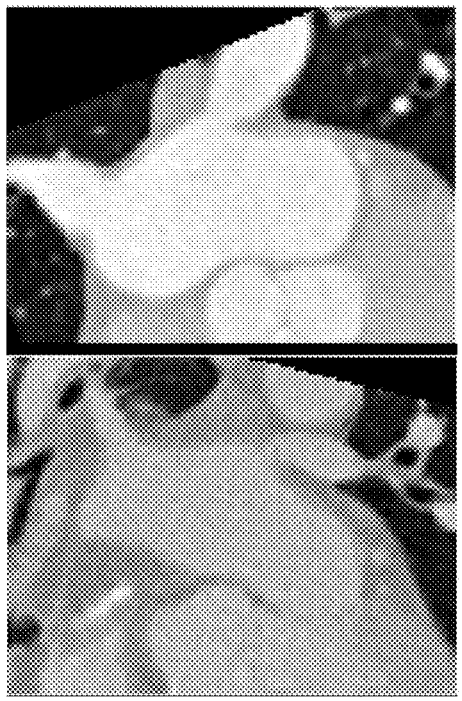
Figure 7D:
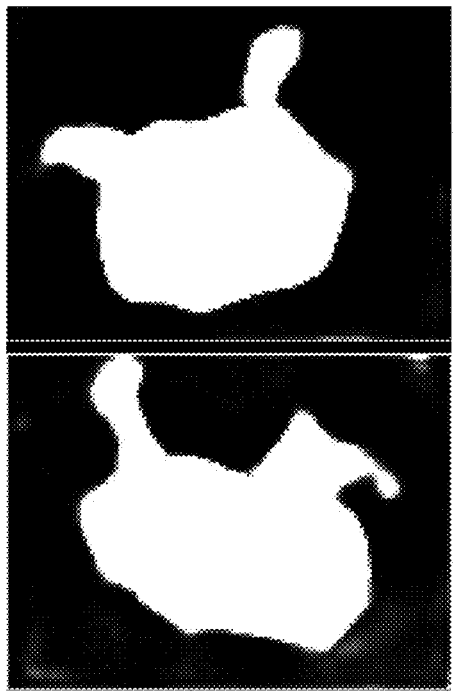
Figure 7E:
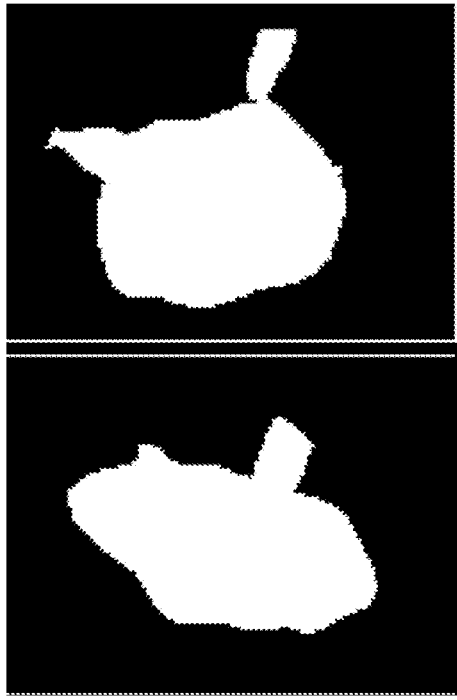

The outputs from the 3D network model are shown in FIG. 7A-E. Each of FIGS. 7A-E show two examples. FIG. 7A shows planar slices through the sparse ICE volume. FIG. 7B shows slices of completed CT volumes output by the 3D network. FIG. 7C shows paired slices of the ground truth CT volumes. FIG. 7D shows predicted 2D segmentation. FIG. 7E shows the ground truth 2D segmentation. The estimated completion outputs do not give as structurally exact results as the "ground truth" but instead try to match the content from the sparse volume. Since the "ground truth" CT volume is paired based on mesh models, this difference is expected and demonstrates that the completion outputs are based on the sparse volume. The system tries to complete the missing regions such that it looks like a "real" CT volume. The performance of the 3D sparse volume segmentation results in the following Dice scores: LA (89.5%), LAA (50.0%), LISPV (52.9%), LSPV (43.4%), RIPV (62.43%), RSPV (57.6%) and overall (86.1%). Using the limited information from sparse volumes, the model still achieves a satisfactory 3D segmentation performance.

The segmentation accuracy may be higher in the region where 2D ICE images are presented. Using the 3D appearance information from the paired CT volumes assists in convergence in training the 3D network.

Figure 8A:
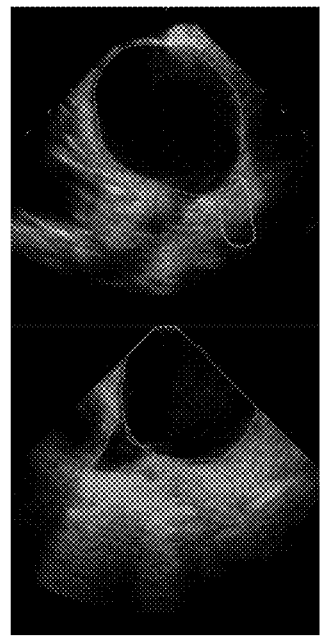
FIG. 8A-D show example 2D segmentations using different approaches, including the method of FIGS. 1 and 4 (FIG. 8D)
Figure 8B:
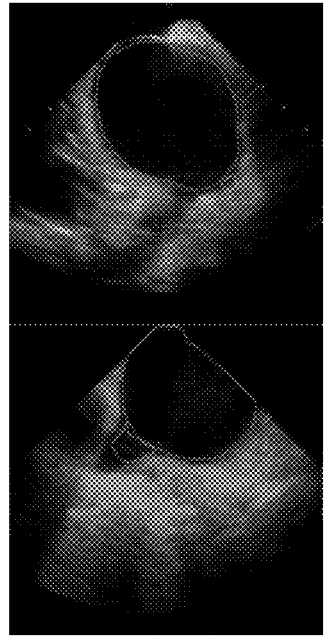
Figure 8C:
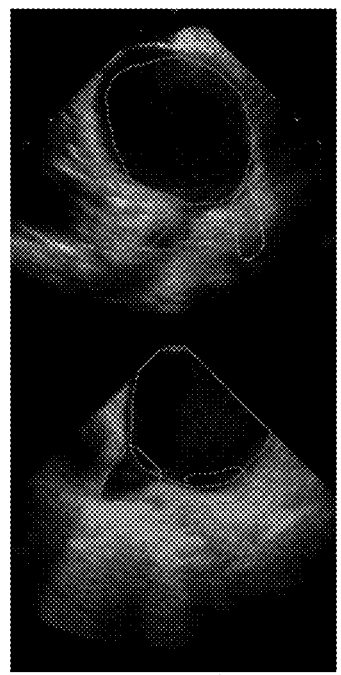
Figure 8D:
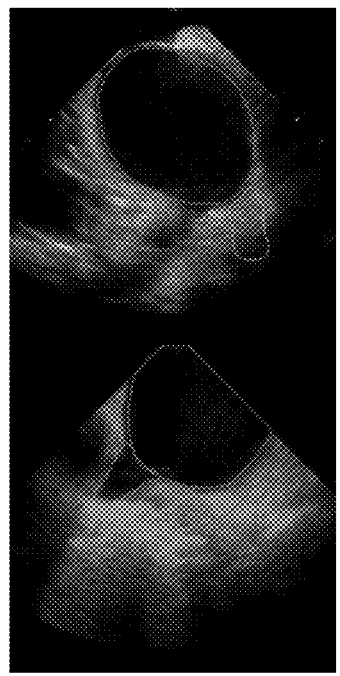

FIGS. 8A-D shows the 2D ICE contouring results using different models: the "2D only" model that is trained directly with the 2D ICE images in FIG. 8B, the "3D only" model by projecting the predicted 3D segmentation results onto the corresponding ICE image in FIG. 8C, and the "2D+3D" model by refining the outputs from the 3D network using the 2D network in FIG. 8D. FIG. 8A shows the ground truth. From the examples in the first row, the "3D only" outputs give better estimation about the PVs than the "2D only" outputs. This is because the PVs in the current 2D ICE view are not clearly presented, which is more challenging to the "2D only" model. The "3D only" model makes use of the information from other views and hence predicts better the PV locations. The outputs from the "2D+3D" model combines the knowledge from both the 2D and 3D models and generally gives superior outputs than these two models. Similar results can also be found in the second row examples where the "2D+3D" model not only predicts the location of the PVs better by making use of the 3D information but also refines the output according to the 2D view.

Quantitative results of these models are given in Table 1:

TABLE 1

| | 2D only | | 3D only | | 2D + 3D | | IRR | |
|---|---|---|---|---|---|---|---|---|
| | Dice | ASSD | Dice | ASSD | Dice | ASSD | Dice | ASSD |
| LA | 94.3 | 0.623 | 93.5 | 0.693 | 95.4 | 0.537 | 89.6 | 1.340 |
| LAA | 68.2 | 1.172 | 66.5 | 1.206 | 71.2 | 1.106 | 68.8 | 1.786 |
| LIPV | 70.1 | 0.918 | 71.7 | 0.904 | 72.4 | 0.856 | 69.9 | 1.459 |
| LSPV | 65.9 | 1.275 | 67.8 | 0.916 | 71.1 | 1.197 | 62.9 | 1.582 |
| RIPV | 69.6 | 0.927 | 71.7 | 0.889 | 73.8 | 0.786 | 71.4 | 1.378 |
| RSPV | 63.3 | 0.872 | 70.4 | 0.824 | 70.5 | 0.862 | 57.8 | 1.633 |
| Total | 91.0 | 0.839 | 89.8 | 0.834 | 92.1 | 0.791 | 88.6 | 1.432 |

The dice metric is a % and the ASSD is in mm. The "3D only" model in general has better performance in PVs and worse performance in LA and LAA than the "2D only" model. This is because LA and LAA usually have a clear view in 2D ICE images, unlike the PVs. The "2D+3D" model combines the advantages of the "2D only" and "3D only" model and in general yields the best performance. The IRR scores from human experts are relatively lower, especially for the LSPV and RSPV. This is expected as these two structures are difficult to view with ICE. The IRR scores are generally lower than those from the models, which demonstrates the benefit of using an automatic segmentation model—better consistency.

Figure 9:
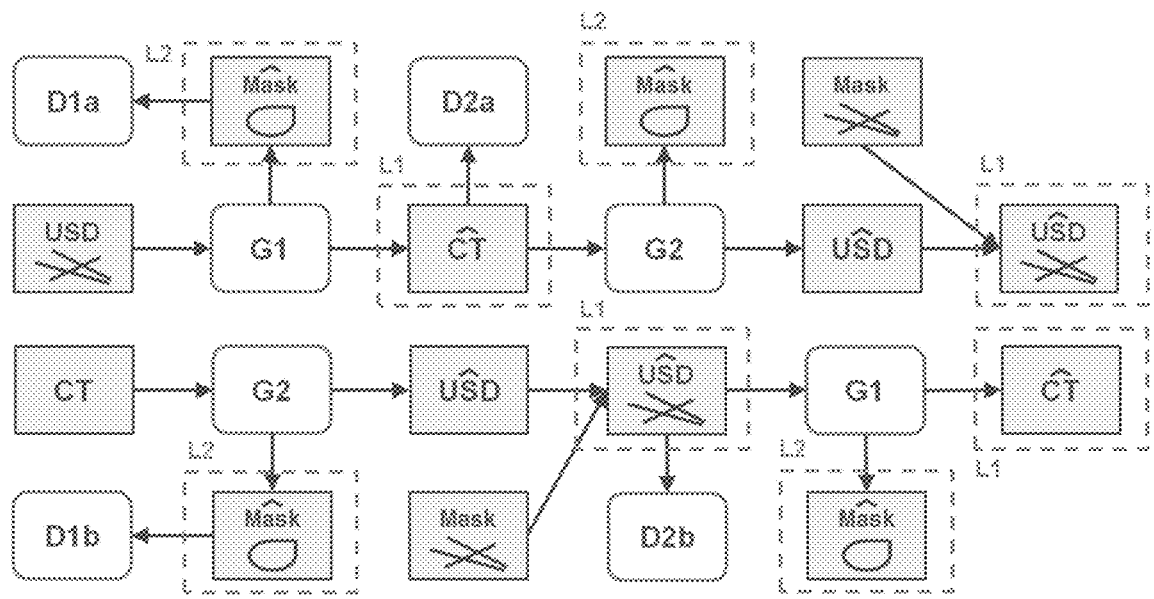
FIG. 9 shows an example of cyclic image-to-image generation.

FIG. 9 shows another network architecture of a cyclic image-to-image generative model for 3D ICE contouring, 3D ICE volume generation and CT synthesis. G is used to designate a generative network, D a discriminator network, and gray as input or output data. The cyclic idea is based on the hypothesis that if a model learns well about the underlying structure of a target domain, the model should be able the convert back to its source domain. In this example, the cyclic model works in two directions: 1) sparse ICE volume to CT volume (and 3D segmentation mask) then CT volume to sparse ICE volume, and 2) CT volume to sparse ICE volume (and 3D segmentation mask) then sparse ICE volume to sparse CT volume.

Figure 10:
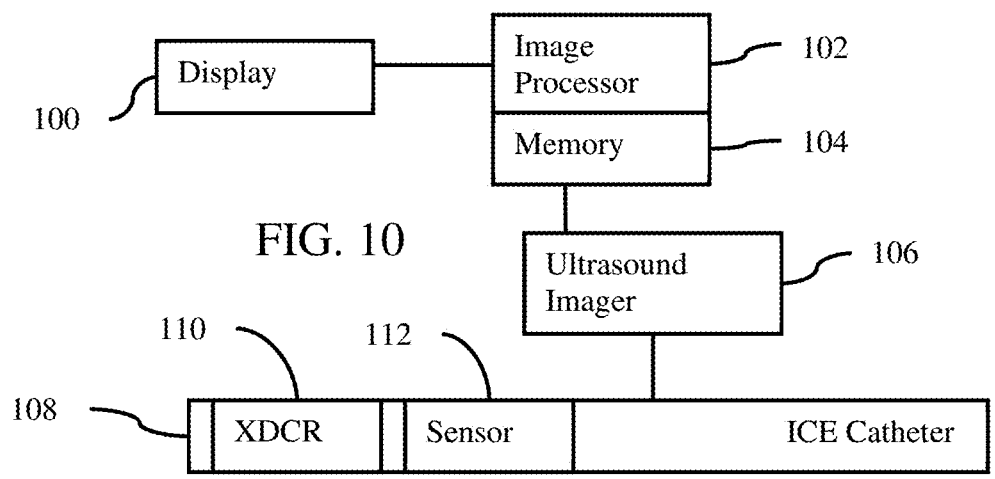
FIG. 10 is a block diagram of one embodiment of a system for 3d segmentation from 2D intracardiac echocardiography imaging in ablation.

FIG. 10 shows a medical imaging system for 3D segmentation from 2D intracardiac echocardiography imaging in ablation. The system generates images on a display 100 to guide ablation. An ablation electrode on a separate or the same ICE catheter 108 is positioned for ablation based on the guidance of one or more images. By showing one or more segmented anatomical structures, the user more likely positions the electrode in the correct location to treat atrial fibrillation.

The medical imaging system includes the display 100, memory 104, and image processor 102. The display 100, image processor 102, and memory 104 may be part of the medical imager 106, a computer, server, workstation, or other system for image processing medical images from a scan of a patient. A workstation or computer without the medical scanner 106 may be used as the medical imaging system. The medical imaging system may also include the ICE catheter 108 with an ultrasound transducer 110 and one or more sensors 112.

Additional, different, or fewer components may be provided. For example, a computer network is included for remote segmentation and image generation of locally captured ultrasound data. As another example, a user input device (e.g., keyboard, buttons, sliders, dials, trackball, mouse, or other device) is provided for user alteration or placement of one or more markers (e.g., landmarks). In yet another example, an ablation catheter and/or catheter guide is provided.

The ICE catheter 108 is a cardiac catheter. The ICE catheter 108 has a small diameter, such as 5-12 mm, is covered in a flexible plastic, and includes guide wires to guide the catheter 108 through the vessels of the patient to place the transducer 110 in the heart or vessel of the patient.

The transducer 110 is a linear array of transducer elements, such as an array of 32, 64, or 128 PZT elements. The transducer 110 is positioned at or near a tip of the ICE catheter 108 to scan a plane normal to the array and extending along a longitudinal or length of the array. The scan plane extends from a side of the ICE catheter 108.

The sensor 112 is a magnetic position sensor, such as three orthogonal coils for sensing change in three dimensions relative to a magnetic field generated external to the patient. One or multiple sensors 112 are positioned next to or on the transducer 110 or at other locations along the ICE catheter 108. The absolute position or change in position are sensed. Other types of sensors 112 may be used, such as an external x-ray or acoustic sensor that senses one or more fiducials or the transducer 110 on the ICE catheter 108.

The ultrasound imager 106 is a medical diagnostic imaging system configured to scan a plane of a patient and generate anatomical information from the scan. 2D ICE images are generated using the transducer 110. As the transducer 110 is moved within the patient, different scan planes are scanned. The beamformers of the imager 106 define sample locations of a field of view in the scan plane and acquire signals for acoustic echoes from the locations. A detector detects the response from the acquired signals. A processor, such as the image processor 102, generates ICE images from the detected data. The ICE images are in a polar coordinate or are scan converted into a Cartesian coordinate system. The ICE images represent the heart or other cardiac anatomy of the patient.

The image processor 102 is a control processor, general processor, digital signal processor, three-dimensional data processor, graphics processing unit, application specific integrated circuit, field programmable gate array, artificial intelligence processor or accelerator, digital circuit, analog circuit, combinations thereof, or other now known or later developed device for processing medical image data. The image processor 102 is a single device, a plurality of devices, or a network. For more than one device, parallel or sequential division of processing may be used. Different devices making up the image processor 102 may perform different functions, such as applying different GANs or applying the GANs and rendering an image. In one embodiment, the image processor 102 is a control processor or other processor of a medical diagnostic imaging system, such as the medical imager 106. The image processor 102 operates pursuant to stored instructions, hardware, and/or firmware to perform various acts described herein.

The image processor 102 is configured to train one or more machine learning networks. Based on a user provided or other source of the network architecture and training data, the image processor 102 learns features for encoders, decoders, discriminators, or other network parts to train the network. A multi-task GAN with two or more discriminators may be trained for 3D segmentation. One task is volume completion and the other task is 3D segmentation. The ground truth for the volume competition is CT or MR volumes from patients different than ground truth for the three-dimensional segmenting. A GAN for 2D segmentation from a projection from the 3D segmentation and from an ICE image may be trained. The result of the training is one or more machine-learned generative or image-to-image network or networks for generating both the 3D segmentation and complete volume from the 2D ICE images and/or for generating 2D segmentation from a 3D projection and 2D ICE image.

Alternatively or additionally, the image processor 102 is configured to apply one or more machine-learned generative networks. For example, a multi-task generator of a GAN is applied to ICE images formed into a volume using relative or absolute positions from the sensor 112. The machine-learned generative network is applied to a sparse ICE volume formed from the 2D ICE images. Based on the previous training, the network generates a 3D segmentation and a more complete (e.g., denser than the input sparser ICE volume) volume representation of the heart. Another network may be applied to output a 2D segmentation from a projection of the 3D segmentation to 2D and an ICE image.

The image processor 102 is configured to generate an image. A rendering of the 3D segmentation and/or the more complete volume with or without one or more 2D ICE images may be imaged. An image may be generated as a slice through the 3D segmentation and/or more complete volume. The 2D segmentation alone or overlaid with the 2D ICE image may be generated. Annotations, coloring, graphics, or other highlighting may be used to show the 2D segmentation or rendered 3D segmentation.

The display 100 is a CRT, LCD, projector, plasma, printer, tablet, smart phone or other now known or later developed display device for displaying the output, such as an image or sequence of images showing 2D and/or 3D segmentation. The display 100 displays ICE images and segmentation to guide ablation. The segmentation assists the user in placing the ablation electrode for atrial fibrillation.

The sensor measurements, ICE images, training data, network definition, features, machine-learned network, 3D segmentation, projection, 2D segmentation, generated images, and/or other information are stored in a non-transitory computer readable memory, such as the memory 104. The memory 104 is an external storage device, RAM, ROM, database, and/or a local memory (e.g., solid state drive or hard drive). The same or different non-transitory computer readable media may be used for the instructions and other data. The memory 104 may be implemented using a database management system (DBMS) and residing on a memory, such as a hard disk, RAM, or removable media. Alternatively, the memory 104 is internal to the processor 102 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 104). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for generating a three-dimensional segmentation mask, the system comprising:
    an ultrasound imager configured to generate two-dimensional intracardiac echocardiography (ICE) images of a part of a cardiac system of a patient with an ICE transducer;
    an image processor configured to generate the three-dimensional segmentation mask from the two-dimensional ICE images using a machine-learned multi-task generative adversarial network; and
    a display configured to display ablation guidance relative to an image of the three-dimensional segmentation mask.

2. The system of claim 1, wherein the machine-learned multi-task generative adversarial network comprises a multi-task architecture with a first task being volume completion and a second task being three-dimensional segmenting, wherein ground truth for the volume completion is computed tomography or magnetic resonance volumes from patients and is different than ground truth for the three-dimensional segmenting.

3. The system of claim 1, wherein the image processor is further configured to generate a sparse volume from the two-dimensional images, wherein the machine-learned multi-task generative adversarial network is configured to input the sparse volume.

4. The system of claim 3, wherein the image processor is further configured to generate a complete volume using the machine-learned multi-task generative adversarial network, wherein the complete volume comprises more voxels than the sparse volume.

* * * * *